(12) United States Patent
Ormsby et al.

(10) Patent No.: US 7,594,913 B2
(45) Date of Patent: *Sep. 29, 2009

(54) RADIO-FREQUENCY BASED CATHETER SYSTEM AND METHOD FOR ABLATING BIOLOGICAL TISSUES

(75) Inventors: Theodore C. Ormsby, Escondido, CA (US); George L. Leung, San Diego, CA (US); Gwo Jenn Shen, Carlsbad, CA (US); Peter Chu, Poway, CA (US); Ming Fan Law, San Diego, CA (US)

(73) Assignee: Medwaves, Inc., San Diego, CA (US)

( * ) Notice: Subject to any disclaimer, the term of this patent is extended or adjusted under 35 U.S.C. 154(b) by 348 days.

This patent is subject to a terminal disclaimer.

(21) Appl. No.: 11/479,259

(22) Filed: Jun. 30, 2006

(65) Prior Publication Data

US 2006/0287649 A1    Dec. 21, 2006

Related U.S. Application Data

(63) Continuation-in-part of application No. 10/637,325, filed on Aug. 8, 2003, now Pat. No. 7,070,595, which is a continuation-in-part of application No. 10/306,757, filed on Nov. 27, 2002, now Pat. No. 7,004,938, and a continuation-in-part of application No. 09/459,058, filed on Dec. 11, 1999, now Pat. No. 6,663,625, which is a continuation-in-part of application No. 09/211,188, filed on Dec. 14, 1998, now Pat. No. 6,190,382.

(51) Int. Cl.
    *A61B 18/18*    (2006.01)

(52) U.S. Cl. .......................... 606/33; 607/101; 607/154; 607/156

(58) Field of Classification Search ..................... 606/33
    See application file for complete search history.

(56) References Cited

U.S. PATENT DOCUMENTS 4,271,848 A * 6/1981 Turner et al. ................. 607/101

(Continued)

FOREIGN PATENT DOCUMENTS

EP          1055399         11/2000

(Continued)

OTHER PUBLICATIONS

International Search Report/Written Opinion issued in PCT/US07/71121—mailed Sep. 9, 2008.

*Primary Examiner*—Lee S Cohen
(74) *Attorney, Agent, or Firm*—Kam W. Li; Procopio, Cory, Hargreaves & Savitch LLP

(57) ABSTRACT

A radio-frequency based catheter system and method for ablating biological tissues within the body vessel of a patient comprises a radio-frequency ("RF") generator for selectively generating a high frequency RF energy signal in a deployable catheter having an RF transmission line, an RF antenna mounted on the distal portion of the catheter, and a temperature sensor also mounted on a distal portion of the catheter for detecting temperature adjacent an ablation site. A control system adjusts the RF energy signal so that the detected temperature is at or close to a selected temperature setting or within a selected temperature range.

43 Claims, 7 Drawing Sheets

U.S. PATENT DOCUMENTS

| | | | |
|---|---|---|---|
| 5,902,251 A * | 5/1999 | vanHooydonk | 600/549 |
| 5,904,709 A * | 5/1999 | Arndt et al. | 607/101 |
| 5,957,969 A | 9/1999 | Warner et al. | |
| 6,067,475 A * | 5/2000 | Graves et al. | 607/101 |
| 6,190,382 B1 | 2/2001 | Ormsby | |
| 6,663,625 B1 | 12/2003 | Ormsby | |
| 7,004,938 B2 | 2/2006 | Ormsby | |
| 7,070,595 B2 | 7/2006 | Ormsby | |

FOREIGN PATENT DOCUMENTS

| | | |
|---|---|---|
| WO | WO 97/26544 | 7/1997 |
| WO | WO 00/35363 | 6/2000 |
| WO | WO 02/26146 | 4/2002 |

* cited by examiner

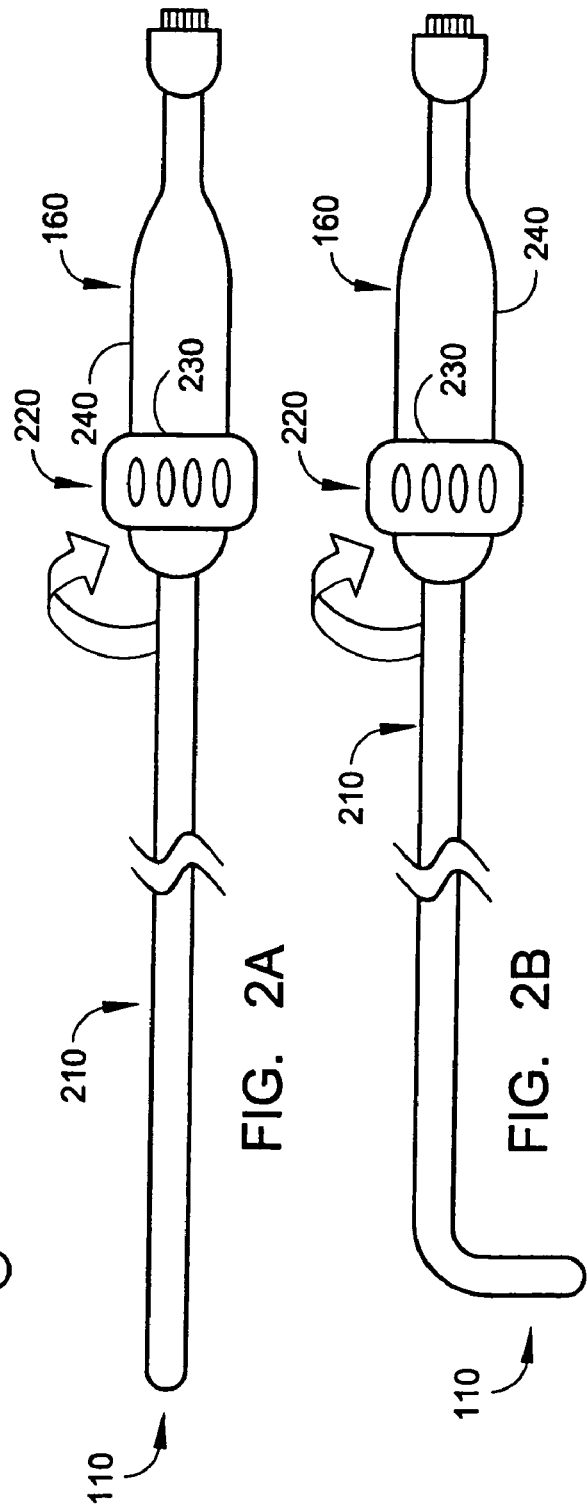

RADIO-FREQUENCY BASED CATHETER SYSTEM AND METHOD FOR ABLATING BIOLOGICAL TISSUES

RELATED APPLICATIONS

This application is a continuation-in-part of U.S. patent application Ser. No. 10/637,325, filed Aug. 8, 2003, now U.S. Pat. No. 7,070,595, which is a continuation-in-part of U.S. patent Application Ser. No. 10/306,757, filed Nov. 27, 2002, now U.S. Pat. No. 7,004,938, and a continuation-in-part of U.S. patent application Ser. No. 09/459,058, filed Dec.11, 1999, now U.S. Pat. No. 6,663,625, which is continuation-in-part of U.S. patent application Ser. No. 09/211,188, filed Dec. 14, 1998, now U.S. Pat. No. 6,190,382. The contents of each of the above identified applications are incorporated herein by reference.

FIELD OF THE INVENTION

The present invention concerns a Radio Frequency (RF) based catheter system for ablating tissue and occlusions, particularly within liquid-filled lumens of animals, such as the heart, liver, arteries and vessels of a human, with an electrical field produced about an RF antenna, and is particularly concerned with a control system and method for controlling RF energy to targeted biological tissue based on preset threshold levels.

BACKGROUND

In recent years medical devices have gained significant acceptance in the medical community as an important treatment modality for heart diseases and other serious ailments, which were traditionally remedied by medication or surgical operation. Two fundamental trends have emerged in the treatment of cardiac diseases. The first has been the shift from open-heart surgical procedures to less invasive and less expensive catheter-based treatments, which are safer and less debilitating.

The second trend is represented by the shift from the use of anti-arrhythmic drugs to minimally invasive catheters or other device-based therapies to palliate incurable arrhythmias. For example, automatic cardioverter-defibrillators are routinely implanted in patients with lethal ventricular arrhythmias to reduce the likelihood of sudden death. Thus, radio frequency (in sub-microwave frequency between 100 kHz to 10 MHz) catheter ablation is now being performed in a large number of patients suffering from cardiac arrhythmias.

Despite these advances in technology, atrial fibrillation ("AF") remains a significant challenge. AF, a rapid irregular rhythm in the atria or upper chambers of the heart induced by non-uniformed electrical pulses, represents a leading cause of stroke and heart attack and a major health care burden. To date, the most effective surgical procedure for the treatment of AF has been the Maze procedure undertaken in "open-heart" surgery. In the Maze procedure, incisions are made along pre-determined lines exterior to the atrium, which are then sutured together. As healing develops, scars are formed along the incision lines thereby forming barriers to the conduction of electrical impulses. By creating such barriers, AF can no longer be sustained and regular heart rhythm is restored. However, the Maze procedure has not been widely adopted due to the morbidity and mortality associated with open-heart surgery, which involves the opening of the chest cavity and cutting of the chest bones.

One new approach to mimic the Maze operation is represented by a catheter-based radio-frequency ablation technique, wherein, instead of surgical incisions, a catheter-electrode is applied to destroy or ablate the heart tissues inside the atrial chamber. The catheter-electrode is passed through the artery for access to the atrium, as commonly practiced in the medical field. Within the atrium, the tip of the catheter-electrode is positioned, usually with the aid of x-ray or fluoroscopic means, and is brought into contact with the heart tissue at a desired location or spot where ablation is required. At this spot, the tissue is destroyed by resistive heating generated from the catheter-electrode. Thereafter, the catheter-electrode is re-positioned to the next spot for ablation. A series of spot ablations thus mimics the lineal lesions as accomplished under the Maze procedure against the conduction of electrical impulses.

Existing catheter-based ablation procedures are recognizably less intrusive than "open-heart"surgery. In addition, during the ablation, disruption of cardiovascular function is reduced. However, a successful catheter-based radio-frequency ablation procedure requires the ablation of tissue spots within the spatial or proximity tolerance between adjacent spots, usually less than 2millimeters, to prevent the passage of electrical impulses. In that connection, the task for the precise placement of the catheter-electrode represents a critical element of a successful procedure.

A major drawback of such existing procedures is the time-consuming task of positioning the catheter-electrode at the desired ablation spots within the atrium while the heart chamber muscles are pulsating. Movements of the atrial wall or the heart muscles often render accurate placement of the catheter-electrode difficult, and slippage of the catheter-electrode tends to occur thereby damaging portions of the atrium where ablation is not desired. As a result, placement of the catheter based RF ablation cannot be efficiently accomplished, and prolonged procedure time, in excess of 12 hours, can be expected. Further, during the procedure, x-ray or other irradiating means are routinely employed for locating and positioning the catheter-electrode, which dictates the use of heavy lead protective gear by the electro-physiologist. As a result, such inconvenience is often amplified by the prolonged procedure time, which detracts from the use of a catheter-based electrode as an efficient means for tissue ablation.

To address these challenges, for example, in U.S. Pat. No. 5,741,249, a catheter-based microwave antenna is disclosed wherein a distal tip is incorporated into the antenna to anchor it to the atrial wall. However, while this design reduces the likelihood of antenna or catheter-electrode slippage during each ablation step, it does not eliminate the consuming task of securing precise placement of the antenna along the desired ablation path for each ablation step. Thus after each ablation step, the antenna has to be re-positioned and anchored precisely at the next spot which must be located within the spatial or proximity tolerance on the ablation path as referenced above.

Accordingly, effective treatments for atrial fibrillation with catheter ablation will require the creation of long or overlapping lineal or curvilinear ablation lesions on the inner surface of the atrium. These lesions can then act as barriers to the conduction of electrical impulses, thus preventing atrial fibrillation.

It is also recognized that a critical requirement for the effective catheter-based ablation of atrial fibrillation is the ability to stabilize and anchor the catheter and microwave antenna inside the atrial chambers. New catheter ablation systems, preferably capable of producing long or overlapping lineal or curvilinear ablation lesions, are required for the development of minimally invasive catheter-based curative procedures for atrial fibrillation.

U.S. Pat. No. 6,190,382, issued Feb. 20, 2001 and U.S. patent application Ser. No. 09/459,058, filed Dec. 11, 2000, both disclose a radio-frequency or microwave-energy based catheter for ablating biological tissues within the body vessel of a patient. The catheter has a proximal portion, a distal portion with a distal end and a lumen extending from the proximal portion to the distal portion. The catheter incorporates an elongated catheter guide that is located within the catheter lumen and is secured to the distal portion of the catheter at one end, with the other end portion extending proximally within the catheter lumen to be coupled to a positioning mechanism. The catheter guide is deployable beyond the distal end of the catheter to form a loop, which is conformable to the interior contour of the body vessel.

The catheter guide carries the catheter with a radio-frequency or microwave energy based antenna incorporated at the distal portion of the catheter. The antenna includes a helical coil, which accommodates the catheter guide passing through it. The radio-frequency antenna is adapted to receive and irradiate radio-frequency energy in the microwave range at a frequency typically greater than 300 Megahertz (MHz) in the electromagnetic spectrum for ablating biological tissue along a biological ablation pathway.

With further improvements to the above-mentioned radio-frequency or microwave-energy based catheter, U.S. patent application Ser. No. 10/306,757, filed Nov. 27, 2002, which is incorporated by reference as though set forth in full and include the same inventors as the present application, discloses advanced deflectable and shapeable structural features of the catheter and particularly its antenna portion. These features substantially enhance the abilities of the electrophysiologists to adapt the form and shape of the catheter and the antenna to conform with the contour of the ablation site and to accurately prescribe the ablation pathway.

SUMMARY OF THE INVENTION

The catheter of the present invention provides further enhancements and features to the catheter described in U.S. Pat. Nos. 6,190,382, 6,663,625, and 7,004,938, and U.S. patent application Ser. No. 10/637,325 filed Aug. 3, 2003. These improvements and features, among others, include a radio-frequency ("RF") generator for selectively generating high frequency RF energy at variable power outputs delivered to the RF antenna. The RF antenna includes a helical coil and has an axial passageway to accommodate the steering control lines.

According to one embodiment the present invention, an improved radio frequency based catheter system is provided for ablating biological tissues of a body vessel, including the atrium of a patient. The system comprises a RF generator in the microwave frequency range adapted for communicating RF energy to a catheter that is adaptable for insertion into the body vessel and a deflectable antenna guide disposed within the catheter lumen. The catheter comprises an RF transmission line and an RF antenna provided at the distal portion of the catheter to receive and transmit radio frequency energy for tissue ablation. After the RF antenna is positioned within the body vessel, the RF generator is activated to apply energy to the antenna. In one embodiment, a controller associated with the RF generator will monitor and minimize reflected to forward power ratio of the antenna and antenna-tissue interface by adjusting the microwave frequency for efficient tissue ablation. In another embodiment of the invention, a temperature sensing system is integrated with the RF antenna and the temperature is monitored and controlled by adjustment of the power setting. Both the reflected to forward power ratio and the temperature may be monitored and controlled within preset limits in a representative embodiment of the invention, although only one of these parameters may be controlled in alternative embodiments.

The temperature changes that are measured by the temperature sensor can be correlated to the combined RF energy effect (ablation) of the biological tissue and the antenna system as a whole. By establishing the set points of the temperatures as measured and adjusting the RF frequency and the power delivered to the target tissue within the preset temperature set points, one can provide an efficient and effective means for tissue ablation.

In a representative embodiment of the invention, the antenna guide includes elongated portions that are secured to control slides for positioning and deployment and deflection control. Alignment of the antenna with the desired tissue ablation pathway is facilitated in one embodiment with the use of radio-opaque markers and/or a radio-opaque antenna element.

After the RF antenna is positioned in the proximity of the body tissue within the body vessel, the RF generator is activated to apply energy to the antenna. The RF generator monitors and minimizes reflected to forward power ratio of the antenna and antenna-tissue interface by adjusting the microwave frequency for efficient tissue ablation.

In one embodiment of the invention, a sensor is deployed to sense the amount of reflected RF energy from the antenna. If the reflected energy is too high, the RF generator will automatically adjust to scale back the frequency of the synthesized waveform in order to maximize energy deliverance to the tissue region.

In another embodiment, the catheter is configured with an RF antenna that integrates a temperature sensing system, and the RF energy delivery to the targeted biological tissue is optimized by controlling both reflected power (reverse power) and the detected temperature.

These and other aspects and advantages of the invention will become apparent from the following detailed description, and the accompanying drawings, which illustrate by way of example the features of the invention.

BRIEF DESCRIPTION OF THE DRAWINGS

The present invention will be better understood from the following detailed description of some representative embodiments of the invention, taken in conjunction with the accompanying drawings, in which like reference numerals refer to like parts, and in which:

FIGS. 1A and 1B are representative side elevation views of an RF ablation catheter of one embodiment of the present invention.

FIGS. 2A and 2B are representative side elevation views of an RF ablation catheter of another embodiment incorporating a handle with a modified steering mechanism;

DETAILED DESCRIPTION OF REPRESENTATIVE EMBODIMENTS

Figure 3A:
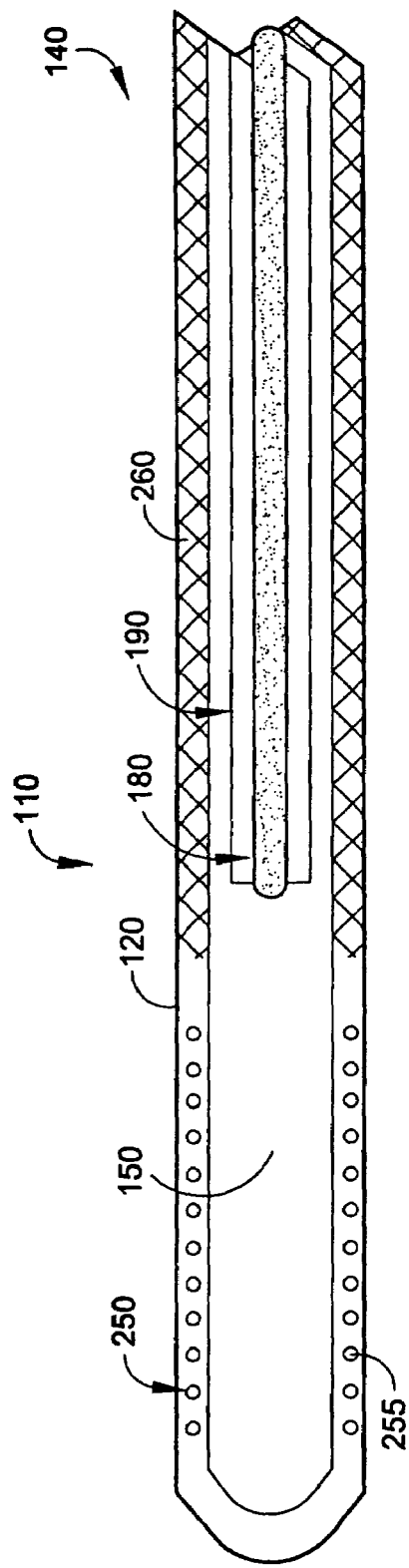
FIGS. 3A and 3B are cross-sectional views of the distal end of the radio frequency based catheter of FIG. 1 or FIG. 2.

Certain embodiments as disclosed herein provide for a radio frequency (RF) based catheter system and method for ablation of biological tissue, and more particularly a system and method which controls RF energy to targeted biological tissue. For example, one method and system as disclosed herein allows for control of RF energy delivery by controlling reflected to forward power ratio, and another method and system as disclosed herein incorporates a temperature sensor for monitoring and controlling reflected temperature in addition to reflected/forward power ratio.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Embodiments of the present invention are deployable for the ablation of biological tissues. Advantageously, these embodiments are adaptable to ablate tissues located in the internal vessels of living mammals by way of a radio-frequency (RF) antenna that is incorporated as part of a catheter. The catheter is insertable within the internal lumens or body vessels of such mammals and the RF antenna is placed in proximity of the tissues to be ablated where RF energy is applied to effect the tissue ablation.

Embodiments of this invention further provide a means for generating a train of RF energy pulses, especially in the microwave frequency range, which are delivered via an electrical transmission line to the RF antenna. The frequency of the RF energy pulses can be selectively varied according to the electrical characteristics of the electrical transmission line and the load impedance associated with the tissue ablation.

In one embodiment, a means for sensing the forward and the reflected powers associated with the microwave frequency energy pulses is provided, so that a reflected-to-forward power ratio may be determined. The output frequency of the energy pulses of the RF generator may then be adjusted to minimize the reflected-to-forward power ratio. This finetunes the impedance of the system energy output to substantially match that of the ablation load and delivers the ablation energy to where it is needed. This provides not only the means for generating and delivering RF energy to the RF antenna for tissue ablation, but also a means to improve the operational efficiency of the RF antenna, which reduces the risks of overheating the electrical transmission line.

In one embodiment of the invention, as illustrated in FIGS. 1A and 1B, a radio-frequency ("RF") ablation catheter 100 includes a shapeable antenna apparatus 110 adaptable for insertion into a body vessel of patient and the shapeable antenna apparatus 110 includes a radio-frequency antenna for delivering electromagnetic energy to a treatment site. The catheter 100 will first be described before describing the shapeable antenna apparatus 110 of the present invention.

The catheter 100 has a flexible elongated tubular body 120 with a proximal portion 130 and a distal portion 140. One or more intracavity lumens 150 (FIGS. 3A, 3B) extend from the proximal portion 130 of the catheter 100 to the distal portion 140. Located at the proximal portion 130 of the catheter 100 is a handle chassis 160 for housing necessary steering and positioning controls, as will be described in further detail below. Incorporated at a proximal end 160 of the catheter 100 is a coupling 170 for connecting the catheter 100 to one or more electronic devices such as an RF generator and control system as illustrated in FIG. 4 for supporting the ablation procedure.

The dimensions of catheter 100 are adapted as required to suit the particular medical procedure, which are well known in the medical art. In one embodiment, the catheter 100 is used to ablate cardiac tissue; however, the catheter 100 may be used to ablate other types of body tissue in alternative embodiments. The tubular body 120 of the catheter may be generally constructed of a polymer material that is bio-compatible within the body vessel environment. Examples of these materials include, but not by way of limitation, Pebax® from Autochem Germany, polyethylene, polyurethane, polyester, polyimide and polyamide, with varying degrees of radiopacity, hardness and elasticity.

The catheter 100 may be formed with a plurality of segments using one or more of the aforementioned materials such that the catheter body 120 is progressively more flexible toward its distal end. The segments may be joined together by thermal bonding, butt joint, or adhesive bonding. Braiding reinforcement can also be added to the circumferential surface of tubular body 120 to attain the desirable level of stiffness and torsional strength for the catheter 100. This allows the catheter 100 to advance and negotiate through the body vessel of a patient, and to enable torque transfer along the length of the catheter from the proximal portion to the distal portion.

Figure 3B:
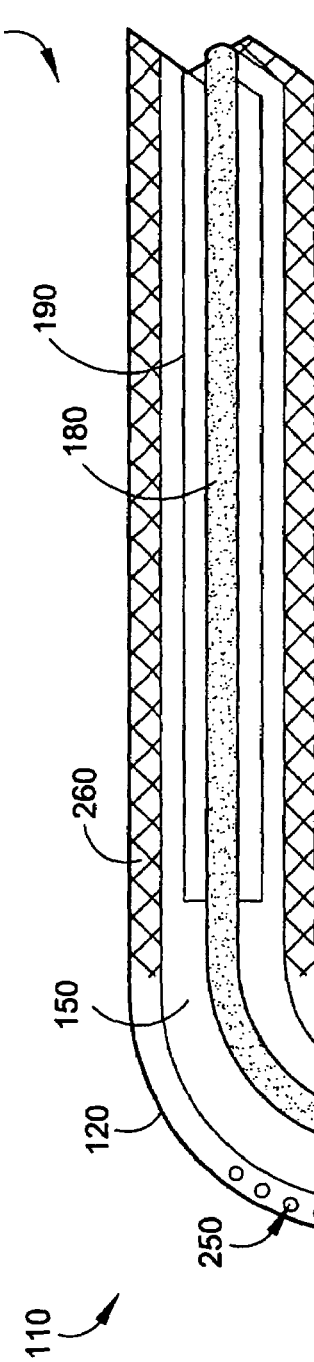
Figure 4:
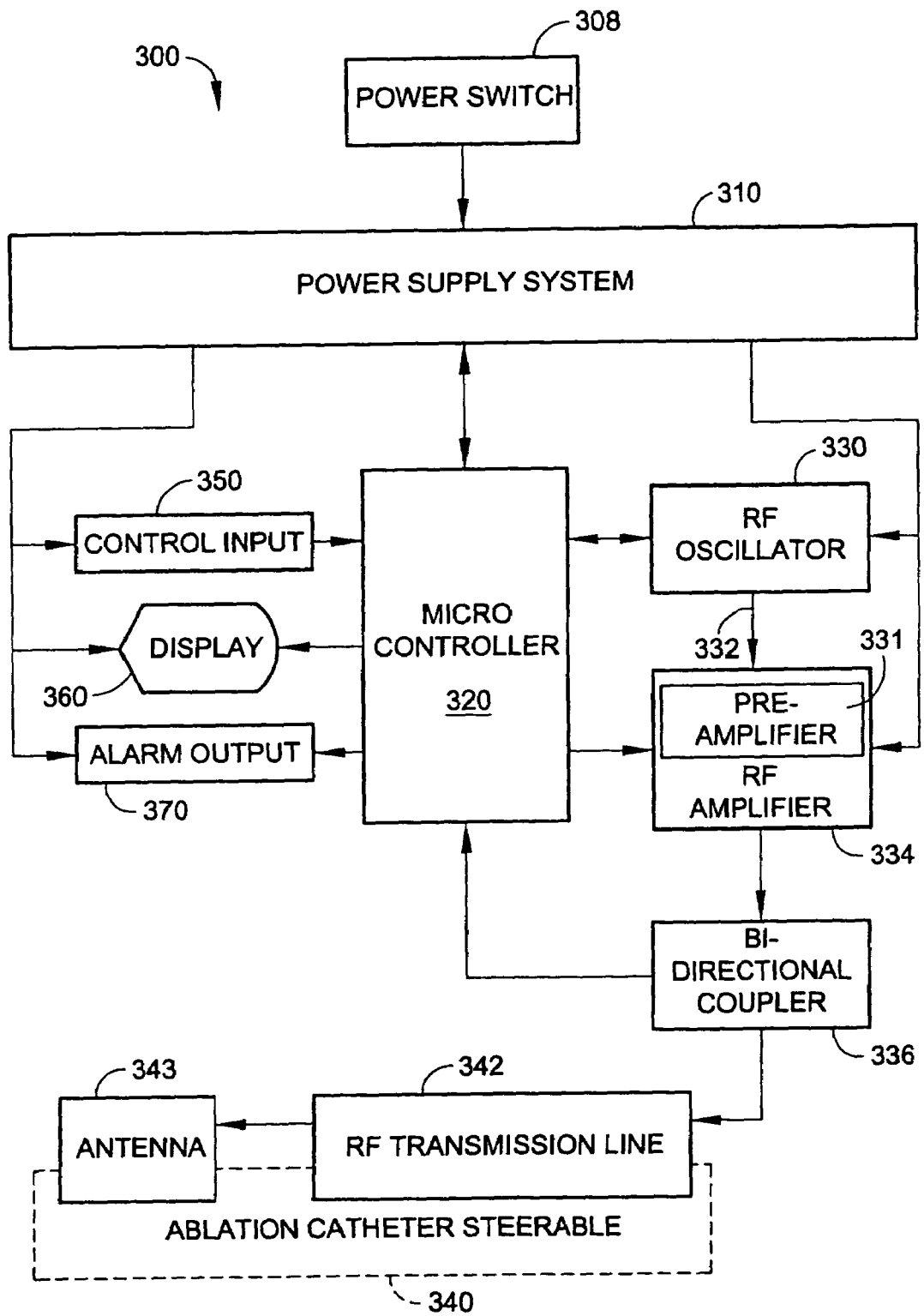
FIG. 4 is a schematic block diagram of a control system for controlling RF energy delivery of the RF ablation catheter of FIGS. 1 to 3 according to a representative embodiment of the invention.

With reference additionally to FIGS. 3A and 3B, the distal portion 140 of catheter body 120 is illustrated in more detail. This portion may include a softer polymer compound than the proximal portion 130, with little or no braiding, to provide the desired flexibility to accommodate distal deflection and shaping of the shapeable antenna apparatus 110. Deflection and shaping of the shapeable antenna apparatus 110 may be implemented through the use of a pre-shaped deflection member 180 and a deflection regulating member 190. The pre-shaped deflection member 180 and/or the deflection regulating member 190 may extend through the catheter body from the handle chassis 160 to the distal portion 140 of the catheter body 140. The distal portion 140 of the catheter body includes an RF antenna 250 having a flexible, helically coiled radiating antenna element 255 for body tissue ablation.

In a representative embodiment, the RF antenna 250 includes an electrically conductive material or wire strip that is wound in a helical fashion to form a flexible, helical coil winding. The appropriate diameter, pitch and length of the coil winding, and the selection of the conductive material or wire strip may vary according to the particular procedure and flexibility requirements. In the illustrated embodiment, the RF antenna is in contact with one or more conductors 260 which extend along the length of the catheter and are connected to the power control system of FIG. 4 via coupling 170. Although the conductors 260 are of flexible mesh or braided wire construction in the illustrated embodiment, it will be understood that these conductors may be of alternative construction in other embodiments, such as thin film electrically conductive material, or elongated, coaxial, circumferentially aligned inner and outer conductors, and the like.

The shapeable catheter apparatus of FIGS. 1, 2, 3A and 3B may carry one or more intracardiac electrocardiogram (ECG) electrodes (not shown) to permit physicians to obtain both optimum tissue proximity and electrical conductive activities before and after tissue ablation. These electrodes may be secured at suitable positions along the length of the catheter.

The pre-shaped deflection member 180 and/or the deflection regulating member 190 may be proximally fastened to deflection control mechanism 220 (FIGS. 2A, 2B) or thumb slide 200 (FIGS. 1A, 1B). In one embodiment, thumb slide 200 is slidably engaged along a axial slot of the handle chassis 160. Axial movement of the thumb slide 200 along the axial slot, together enables a physician to shape or deflect the shapeable antenna apparatus 110 between a straight configuration (FIG. 1A) and a deflected, shaped configuration (FIG. 1B), or any configuration therebetween. A frictional capture mechanism (not shown) may be incorporated in the thumb slide 200 to maintain the grip position in the axial slot. Many such means are commercially available. Examples of such means include set-release, pressure switch or self-locking mechanisms.

FIGS. 2A and 2B illustrate an RF ablation catheter 210 similar to the RF ablation catheter 100 described above, but with an alternative embodiment of a deflection control mechanism 220 for shaping or deflecting the shapeable antenna apparatus 110. The deflection control mechanism 220 may include a rotatable collar 230 that circumferentially surrounds and is rotatably coupled to a handle shaft 240 of the handle chassis 160 to control axial movement of the pre-shaped deflection member 180 and/or the deflection regulating member 190. The handle chassis 160 may house a translation mechanism that translates rotation movement of the collar 230 to axial movement of the pre-shaped deflection member 180 and/or the deflection regulating member 190. Rotational movement of the collar 230 relative to the handle shaft 240 enables a physician to shape or deflect the shapeable antenna apparatus 110 between a straight configuration (FIG. 2A) and a deflected, shaped configuration (FIG. 2B), or any configuration therebetween.

FIG. 4 is a schematic block diagram of a control system 300 for controlling the RF output signal from the ablation catheter of FIGS. 1 to 3 according to an embodiment of the invention. FIG. 4 illustrates the electrical and signal components of the system. Catheter system 300 has a power switch 308, power supply system 310, micro-controller system 320, RF signal generator or oscillator 330, RF amplifier 334 comprising a pre-amplifier 331, RF bi-directional coupler 336, control input 350, display 360, and alarm output 370. The bi-directional coupler 336 is connected to the distal end of RF transmission line 342, and the proximal end of the transmission line is connected to RF antenna 343. The transmission line 342 and antenna 343 are incorporated in a steerable ablation catheter 340. In one embodiment, ablation catheter 340 may be identical to the ablation catheter 100 of FIGS. 1 to 3, and antenna 343 may be the coiled RF antenna 250 of FIGS. 3A and 3B while the transmission line 342 comprises electrical conductors 260.

The RF based catheter system 300 is powered by ordinary alternating current power and it could be adapted to be powered by an appropriate direct current source as well. The power switch 300 connects the electrical power to the system power supply 310. The system power supply provides primary patient safety isolation and synthesizes various direct current voltages necessary to operate the apparatus to effect tissue ablation.

The microcontroller 320, which is microprocessor based, provides for user input, displays for inputs and outputs, and sets system alarm conditions. Microcontroller 320 also monitors and controls RF power synthesis and communication to the RF antenna 343 and ablation tissue. As shown in FIG. 4, the microcontroller 320 monitors and controls RF signal oscillator 330, which receives power from the power supply system 310. RF signal oscillator generates a continuous RF frequency wave signal 332 at a power level and frequency determined and controlled by micro controller 320.

In the embodiment of the present invention, the RF signal oscillator 330 is electrically coupled to the power amplifier 334. The power amplifier 334 includes a preamplifier 331, which initially amplifies the wave signal 332 from the RF generator and produces a first train of relatively low energy pulses. After amplification by RF amplifier 334, the energy pulses are then delivered via a transmission line 342 to an RF antenna 343, which is placed in the proximity of the tissue to be ablated.

As shown in FIG. 4, the bidirectional coupler 336 is electrically interposed between the amplifier 334 and transmission line 342. The coupler samples the relatively low energy forward pulses along the transmission line and the energy pulses reflected from the target ablation tissue and uses the signal samples as feedback to the micro controller 320. The feedback mechanism provided by sampling the signal at the coupler 336 is useful for scaling back the amount of reflected energy. Too much signal reflection could potentially destroy sensitive system 300 components or cause patient injury.

Electrically in communication with the bi-directional coupler 336, the micro-controller 320 monitors the forward and reflected energy pulses. Micro-controller 320 then defines a ratio for the reflected and forward energy pulses. In one embodiment, this ratio comprises a voltage standing wave ratio (VSWR), computed as:

$$VSWR = \frac{1 + |\Gamma_0|}{1 - |\Gamma_0|}$$

where $\Gamma_0$ represents the load reflection coefficient computed using the appropriate boundary conditions along RF transmission line 342.

A low ratio would indicate that most of the energy generated by the system is applied to the load for ablation, and is characteristic of having achieved matched impedance between the apparatus and the ablation load. A high ratio, on the other hand, would indicate that a significant amount of the energy generated by the system is being reflected, and is characteristic of a high degree of return loss, or leakage, resulting from a poor impedance match.

To the extent that the impedance of RF transmission line 342 is affected by the pulse 332 frequency, one embodiment provides a means to enable the change of frequency in the power output of the system such that both the line impedance and the load impedance will be matched. The means for sensing (i.e., the bi-directional coupler, in one embodiment) and the means for adjusting comprise a means for adjusting RF signal source 330 and RF power amplifier 334 in response to the means for controlling (i.e., the micro controller 320) to match the transmission line impedance to the load impedance. For example, if the ratio indicates that too much energy is being reflected (e.g., VSWR is high), the micro controller 320 adjusts the frequency of the RF signal 332 generated by the oscillator 330 to effect a reduced value in the ratio of the reflected and forward energy pulses. Such a reduction in the power ratio effects impedance matching between the transmission line and the ablation load. An acceptable amount of return loss would depend upon the application. However, since a perfect impedance match is never achievable, micro controller 320 can allow for the user to adjust the frequency such that the ratio drops below some threshold value. The threshold value may be below 1.4:1, and in one embodiment the threshold value is 0.4:1.

Because load impedance can vary widely among tissue types and can vary according to the quality and quantity of fluids surrounding the tissue, such as in a blood-filled cavity or chamber, the means for controlling supports a broad range of frequency adjustment settings to enable flexible deployment of system 300 in the field.

Having achieved a match in the impedance, the microcontroller 320 adjusts the power amplifier 334 to produce the train of relatively high energy pulses, which will be delivered via the transmission line to the RF antenna to effect tissue ablation. In one example of the present invention, the power level generated for ablation process was approximately 60 watts.

In addition to providing monitoring and adjusting functions over the frequency of the RF pulses, the micro-controller 320 also communicates the various signals and indicators to a user such as electro-physiologist. The system supports manual override in the RF frequency, output power, and setting the ablation duration. In a typical configuration, the control input 350 of the present invention may be equipped with a multi-line display, a set of up and down keys for adjusting output power level and ablation period, a ablation on/off key for activating ablation processes, and a mode/setup key for changing display mode and/or configuring an I/O port.

The output power level of the RF amplifier 334 is monitored continuously during ablation processes. The RF bi-directional coupler 336 provides the ability to sample both forward and reverse power levels at attenuated levels that are electrically connected to the micro-controller assembly. The micro-controller assembly compares the two signals and adjusts both the signal source and the preamplifier/power amplifier gains to achieve lowest reverse-to-forward power ratio.

The RF based catheter system 300 monitors and controls the microwave frequency and power output within typical range of 900 MHz to 930 MHz to minimize reflected-to-forward power ratio. The RF antenna 343 is typically manufactured and tuned to 915 MHz in the saline solution closely approximating biological tissue and fluid filled animal body vessel to be ablated. Upon entering the body vessel and coming in contact with the biological tissue to ablation, the electrical dimension of the RF antenna 343 may slightly altered temporary to cause reflected power to increase. Increased reflected power reduces overall power available for irradiation and therefore, reduces efficient tissue ablation. If the reflected power is left unchecked and increases greatly, local heating of the RF antenna 343 may occur and produce unwanted ablation affects.

Figure 5:
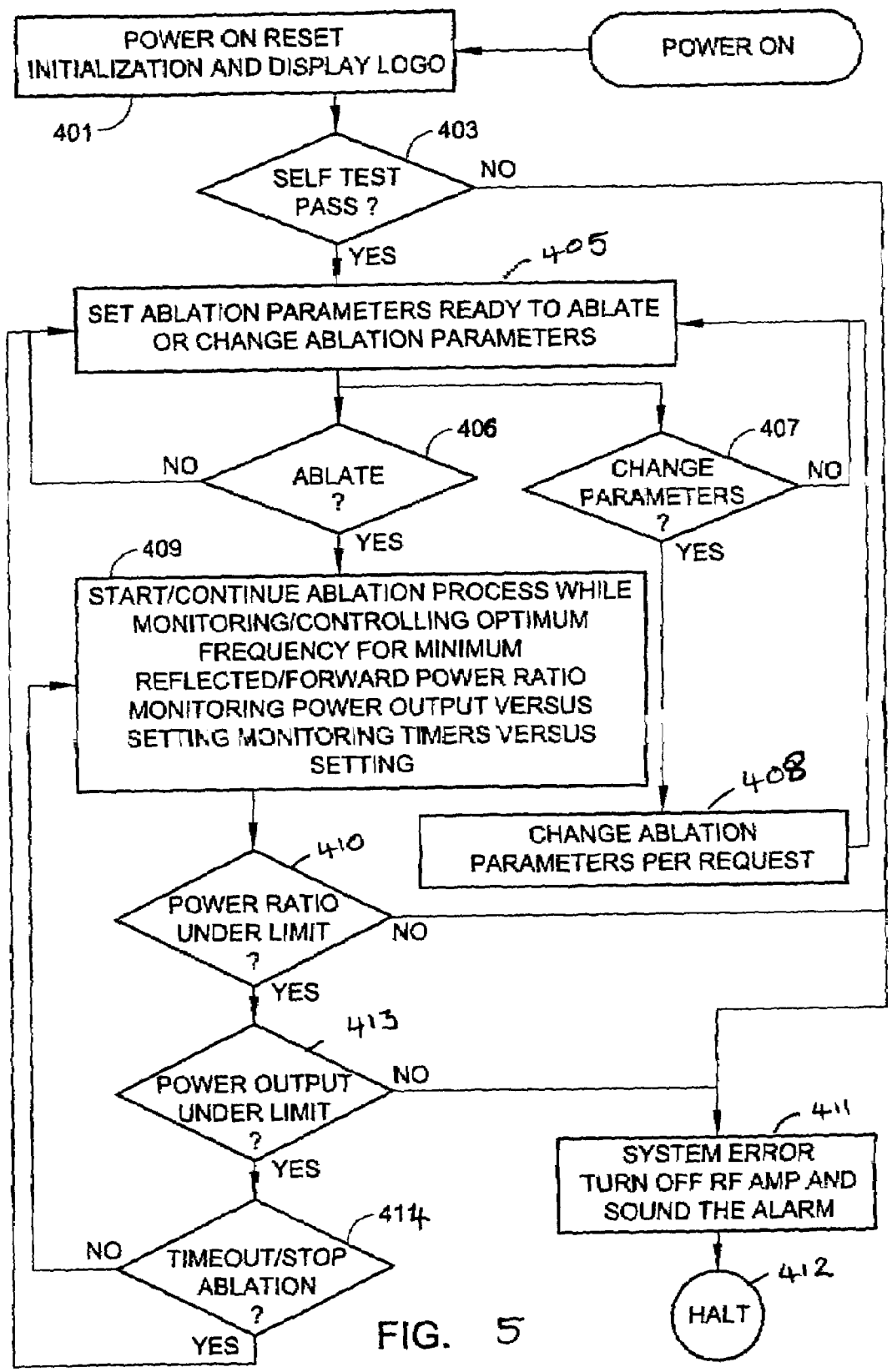
FIG. 5 is a flow diagram illustrating a method of establishing and controlling microwave frequency to minimize reflected to forward power ratio in the system of FIGS. 1 to 4.

FIG. 5 is a flow diagram of a method for biological tissue ablation according to an embodiment of the invention. Such a method can be used to program the instruction set of microcontroller 320 in order to carry out the ablation procedures described herein.

The process begins after the system is powered on by a user, usually by engaging power switch 301. In step 401, the system normally runs a battery of initialization routines in order to establish system integrity. Self-test can comprise, for example, displaying a logo on a display and checking system ROM for appropriate hardware.

In condition block 403, the process branches to a system error if the power-on self test fails. In one embodiment, if the self-test fails on power-on, then an alarm 370 will sound.

If the self-test passes in condition block 403, then ablation parameters can be set either automatically, or manually by the electro-physiologist in step 405. In one embodiment, the ablation parameters are ablation power and ablation time period. Previously set ablation parameters can be changed in steps 407 and 408. Once ablation parameters have been set, the operator can choose whether to start the ablation process (step 406). On initiating the ablation process, ablation is carried out under continuous monitoring conditions (step 409), so that an appropriate adjustment can be made to the frequency of oscillator 330, such as in the case that the measure of reflected-to-forward power is too high. Several parameters can be monitored in real-time to insure that critical system thresholds are not exceeded. For example, in step 409, power output can be monitored as well as reflected/forward power ratio, to insure that the prescribed amount of ablation exposure is provided. Too much exposure, and unwanted results, such as ablation of surrounding benign tissue, could result.

If the reflected/forward power ratio detected to be over the pre-set limit (step 410), the RF amplifier is turned off and the system alarm is sounded (step 411) at alarm output 370 of FIG. 4, and the ablation procedure is stopped (412). If the ratio is below the pre-set limit, but the power output is over a pre-set limit (step 413), the RF amplifier will again be turned off and the alarm sounded (step 412). However, as long as both the power ratio and power output are within the pre-set limits, the ablation process will continue until the ablation time out is reached (step 414), after which the system will return to step 405 and await input of ablation parameters for a subsequent ablation procedure. The user will set the ablation time period as one of the parameters entered at step 405. Any suitable alarm output may be provided, including audio, visual, or both.

Figure 6A:
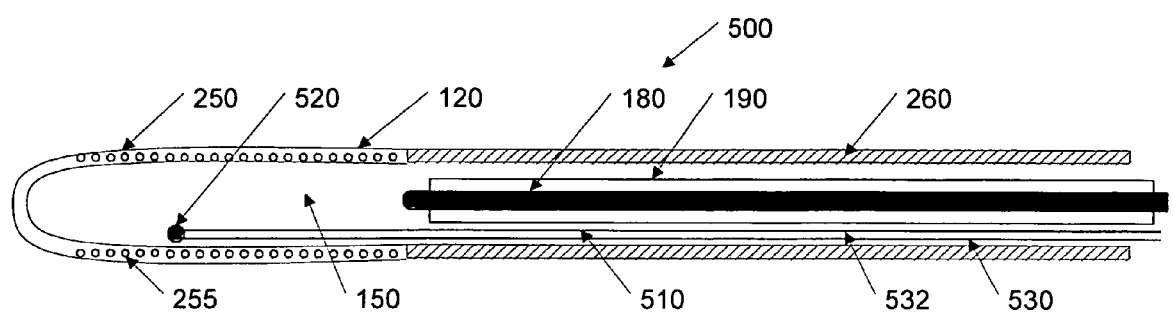
FIGS. 6A and 6B are cross-sectional views similar to FIGS. 3A and 3B but illustrating a modified RF ablation catheter according to another representative embodiment of the invention, the catheter incorporating a temperature sensor.
Figure 6B:
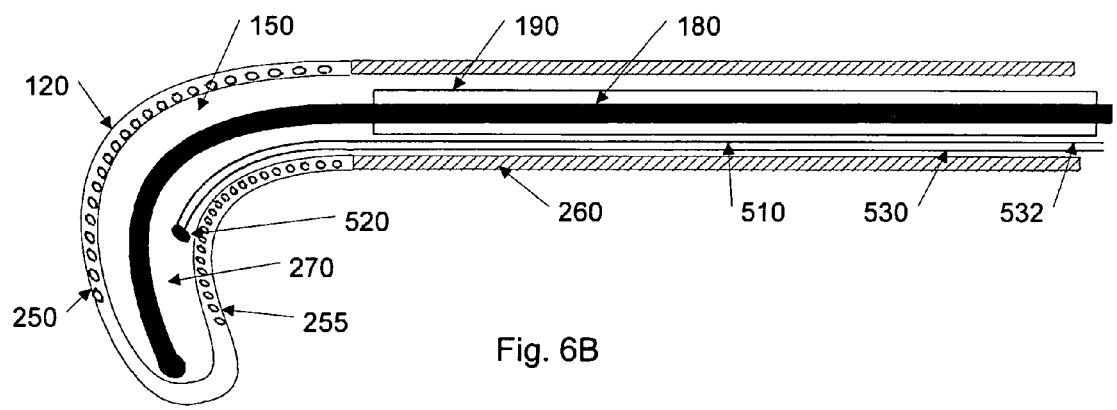

FIGS. 6A and 6B illustrate the proximal end of an ablation catheter 500 according to another embodiment of the invention. The ablation catheter 500 is similar to catheter 100 of FIGS. 1 to 3 but additionally includes a temperature sensor 510. Catheter 500 is otherwise identical to the catheter 100 of FIGS. 1 to 3, and like reference numerals have been used for like parts as appropriate. The temperature sensor 510 may be a thermistor, thermocouple, or the like, and has a sensor end or thermocouple junction 520 adjacent the distal end of the catheter 500, and a pair of conductors 530, 532 extending from the junction 520 through the catheter lumen 270 to the proximal end of the catheter, where they are suitably connected to control circuitry as described in more detail below with reference to FIGS. 7 and 8. Although the temperature sensor 510 is mounted inside the catheter in the embodiment of FIGS. 6A and 6B, it will be understood that it may be secured along the outside of the catheter or embedded in the catheter wall in alternative embodiments.

Figure 7:
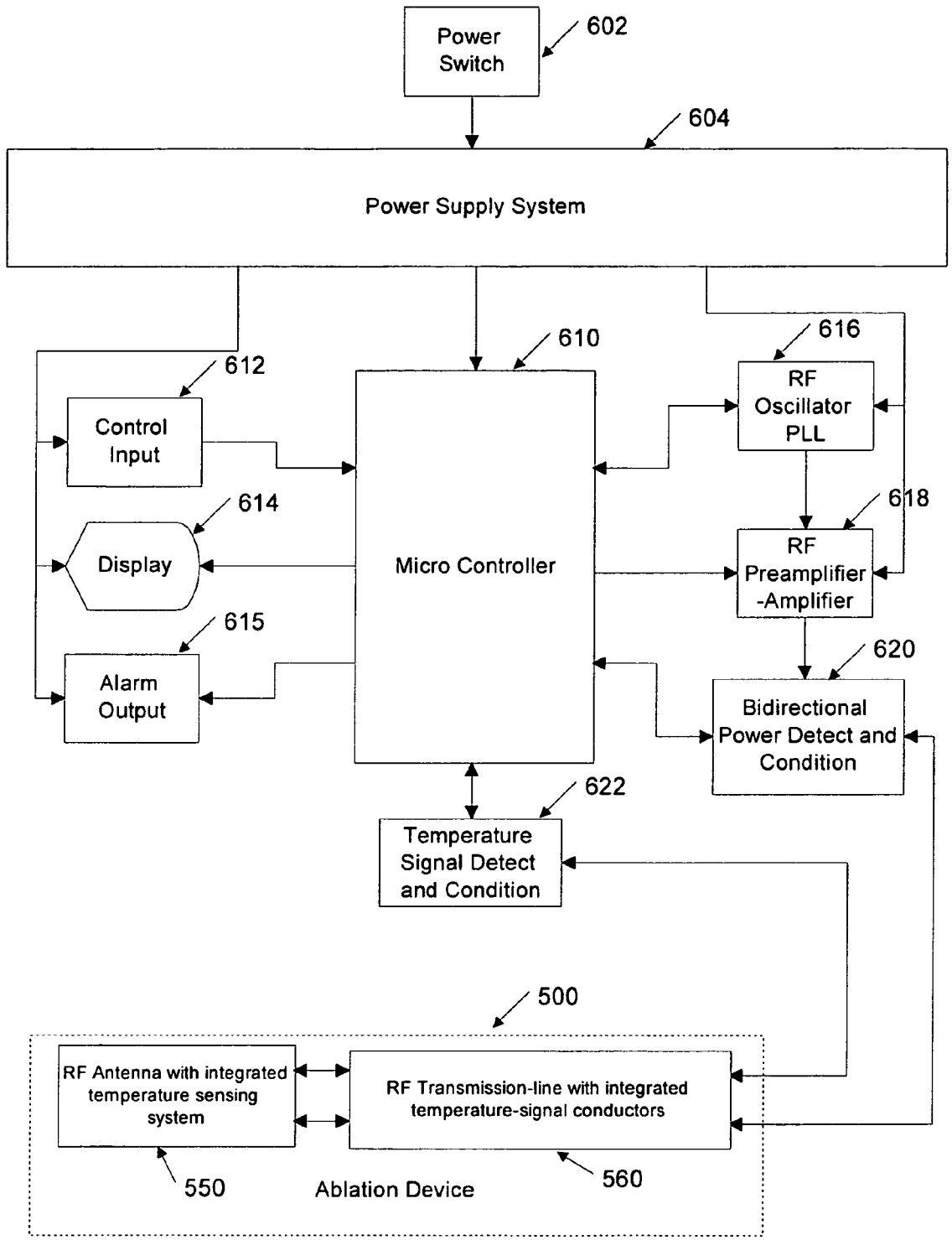
FIG. 7 is a schematic block diagram of a power and temperature control system according to a representative embodiment of the invention, incorporating the RF ablation catheter of FIG. 6.
Figure 8:
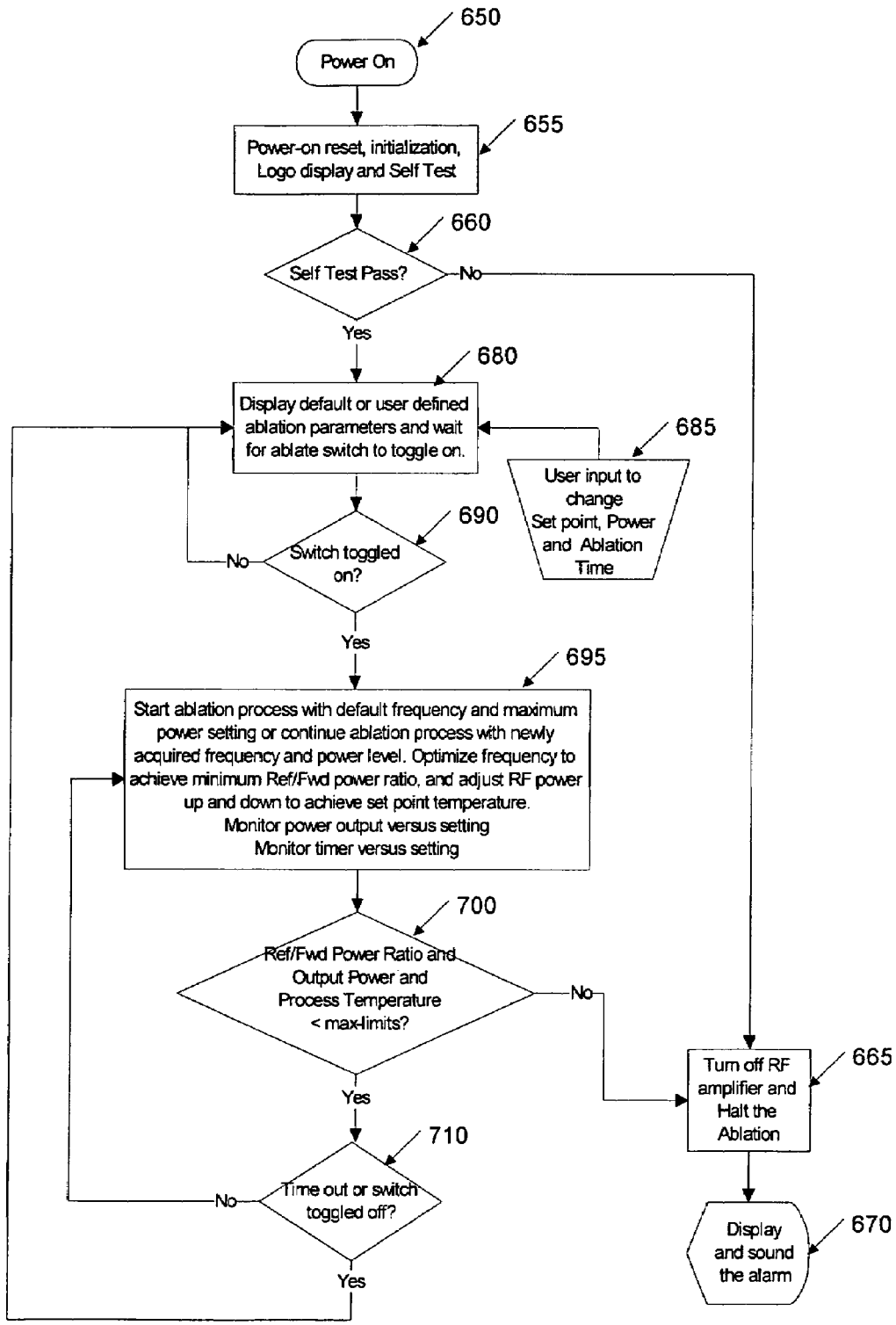
FIG. 8 is a schematic flow diagram illustrating the method of controlling reflected power and tissue temperature in the system of FIG. 7.

FIGS. 7 and 8 illustrate a control system 600 and associated method for monitoring and controlling reflected/forward power ratio, power output, and temperature in an RF ablation catheter incorporating a temperature sensor, such as catheter 500 of FIGS. 6A and 6B. System 600 has a power switch 602, and a power supply system 604 which may be identical to the power supply system 310 of FIG. 3 and which supplies power to various components of the system as illustrated in FIG. 7, including a microcontroller 610 for controlling operation of the system according to programmed instructions and operator input at control input 612. A display module 614 and output alarm module 615 are connected to appropriate outputs of microcontroller 610.

Microcontroller 610 is also connected to an RF signal generator or oscillator 616, which may be a phase-locked loop (PLL) oscillator. The RF signal oscillator 616 is connected to power amplifier 618, which includes a preamplifier for initially amplifying the output signal from RF oscillator 616, and a second RF amplifier for final amplification of the signal. After amplification by the RF amplifier 618, the pulsed RF signal is delivered through bi-directional coupler 620 to RF transmission line 560 of the ablation device 500. As in the control circuit of the previous embodiment (FIG. 4), the bi-directional coupler 620 samples the relatively low energy forward pulses transmitted along the transmission line to the RF antenna 550 and the energy pulses reflected back from the target ablation tissue, and provides the forward and reflected pulse samples as feedback to the microcontroller 610. A temperature signal detect and condition module 622 is connected to the temperature signal conductors 530, 532 (see FIGS. 6A, 6B) at the end of RF transmission line 560, and module 622 is also connected to microcontroller 610.

As in the previous embodiment, the microcontroller is programmed to monitor the power output and the forward and reflected energy pulses, and to compute the ratio between the forward and reflected energy pulses, or the voltage standing wave ratio VSWR as defined above in connection with the control system in the embodiment of FIGS. 4 and 5 above. Additionally, in this embodiment, the microcontroller is also programmed to monitor the temperature detected at temperature sensor 520 which is closely related to the temperature induced in the tissue as a result of the ablation process, since the temperature sensor 520 is located close to the ablation site. It will be understood that temperature sensor 520 may be mounted on the outside surface of the catheter or at the tip of the catheter in alternative embodiments.

In the embodiment of FIGS. 7 and 8, the microcontroller 610 is programmed to adjust the frequency to achieve a minimum reflected to forward power ratio, as in the previous embodiment, and to adjust the RF power level to achieve a selected temperature setting. The temperature setting may be a temperature set point, plus or minus a few degrees, or may be a selected temperature range, as described in more detail below in connection with the flow diagram of FIG. 8. The reflected power is proportional to the combined impedance of the biological tissue and the antenna system as a whole, and therefore minimizing the reflected power is the same as impedance matching the system for maximum transfer of forward power for delivery to the tissue being ablated. At the same time, the temperature changes that are measured by the temperature sensor can be correlated to the combined RF energy effect (ablation) of the biological tissue and the antenna system as a whole. By establishing the set points of the temperature as measured and adjusting the RF frequency and the power delivered to the target tissue within the preset temperature set points, one can provide an efficient and effective means for tissue ablation. Although this embodiment uses both the detected temperature and reverse to forward power ratio as control parameters in adjusting the RF signal parameters in order to achieve a temperature and a power ratio close to user or default settings, alternative embodiments can use temperature alone as the control parameter. The microcontroller may also monitor the output power and temperature to ensure that they do not exceed maximum limits for safe operation.

In the system of FIGS. 7 and 8, the microcontroller adjusts the RF frequency by controlling oscillator 330, thereby also adjusting the reflected/forward power ratio. RF power delivered can be adjusted up and down by controlling amplifier 618, in turn adjusting the reflected temperature. The flow diagram of FIG. 8 illustrates the steps in an ablation procedure according to an embodiment of the invention, using the control system of FIG. 7 along with an RF ablation catheter incorporating a temperature sensor, for example as in FIG. 6. The power is first switched on at switch 602 (step 650) and a power on reset, initialization, and self-test procedure is then carried out (step 655). In this step, the system runs a battery of initialization routines in order to establish system integrity, as described above in connection with step 401 of FIG. 5. If the self test fails (condition block 660), the RF amplifier will be turned off and the ablation procedure will be halted (step 665), and the alarm will be displayed and sounded (step 670). If the self test is successful, the default or previous user selected parameters will be displayed on display module 614, and the system will wait for the user to toggle on an ablation switch before starting the ablation process (step 680).

Ablation parameters can be adjusted or set by an operator at input module 612 at the start of an ablation procedure (step 685). The parameters which can be varied by the operator are a temperature set point, power level, frequency, and an ablation time period. The desired parameters will vary depending on the targeted biological tissue and other factors. The system will include default starting values of frequency and power level, and both will be adjusted as necessary to achieve the lowest possible reverse/forward power ratio and a process or detected temperature at sensor 520 close to the temperature set point. In addition to the pre-set or operator selected operating power level, temperature level, frequency, and ablation time period, the system also has fixed maximum limits of power ratio, power and temperature for safe operation which are independent of the control loop. The maximum power ratio, power level and temperature represent the maximum limit that the catheter can withstand, for safe operation of the system.

As noted above, the operator can vary the set point temperature or temperature range, power level, frequency, and ablation time period by changing the settings on the control input 612 at step 685. The temperature setting input by an operator may be a specific temperature or a temperature range. Where the input is a specific temperature, the system controls the RF signal pulses so that the detected temperature is equal to the specific temperature selected by the operator, plus or minus a few degrees. Where the input is a temperature range, the system controls the RF signal pulses so that the detected temperature is within the selected range. The set point temperature or temperature range selected may be within the range from 45 degrees Celsius to 125 degrees Celsius, and the exact temperature setting will depend on the targeted biological tissue. For example, in the heart, the temperature setting or set point may be in the range from 50 to 90 degrees Celsius. In non-intracardiac tissue, such as the liver, outer surface of the heart, or other non-intracardiac tissue regions, the temperature setting or set point may be in the range from 60 to 120 degrees Celsius, for example. The system may have recommended temperature levels or ranges for different types of biological tissues for operator reference purposes. In step 695, the microcontroller will vary the RF frequency to achieve and maintain the lowest possible reverse/forward power ratio and adjust the RF power level up or down from the set point to achieve a temperature at or close to the set point or within the set point range (where the temperature setting is a range rather than a specific temperature). At the same time, the power output, temperature and timer will be monitored and compared to the settings and to the system maximum limits for output power and process temperature.

As noted above in connection with the previous embodiment, it is desirable for tissue ablation purposes to match the transmission line impedance as closely as possible to the load impedance. If the ratio of reverse to forward or input power is too high, it indicates that too much energy is being reflected, i.e. not being absorbed by the tissue, and the signal frequency is adjusted to produce a reduced power ratio. Because a perfect impedance match is not likely in practice, the frequency and power level are adjusted by the microcontroller in step 695 to achieve the lowest possible level within the constraints of the selected ablation temperature set point. As in the previous embodiment, a threshold level for the ratio may be set, such as 0.4:1, and the controller can then adjust the frequency until the ratio drops below this value. In an alternative embodiment, as noted above, the power ratio is not used and the system controls the frequency and power level of the RF signal to maintain the selected temperature setting.

In the illustrated embodiment, the RF frequency and power level are varied in order to achieve a temperature as close as possible to the selected temperature set point while maintaining a desired ratio of reflected to forward power. The detected temperature at sensor 510 will be indicative of the combined RF energy effect on the biological tissue. Controlling the temperature to be at or close to a set point may therefore improve or optimize tissue ablation.

As noted above, the system has maximum limits set for the power ratio, power level, and temperature level, and will stop the ablation process if any of these limits is exceeded (step 700). In the event that one of the maximum limit values is exceeded, the RF amplifier is turned off and the ablation process is halted (step 665) and, in step 670, the system will display and sound the alarm 615. As long as the power ratio, power level and temperature are within the maximum limits, the ablation process will continue for the pre-set time period or until the ablation switch is toggled off (step 710). When the ablation time period expires or the ablation switch is turned off by the operator, the system returns to step 680, displaying the default or previous user defined ablation parameters and awaiting further input by the user or operator.

In this embodiment, the ablation device or catheter is configured with an RF antenna that integrates a temperature-sensing system for more precise control purposes, and also to reduce the risk of excessive temperatures and the like. The RF energy delivery to targeted biological tissue is optimized by controlling both the reflected/forward power ratio, and the reflected tissue temperature, by monitoring the temperature sensor output and varying the power level to achieve a temperature at or close to a selected set point. It is necessary to adjust both the RF frequency and signal power levels to achieve the desired biological tissue effects and therefore the reflected/forward power ratio and detected temperature are interdependent in achieving control of the ablation process. The reflected power echoes the combined impedance of the biological tissue and antenna system as a whole, and therefore minimizing the reflected power to forward power ratio is equivalent to impedance matching the system for maximum transfer of forward power delivery to the biological tissue being ablated. The temperature changes that are measured by the temperature sensor can be correlated to the combined RF energy effect (ablation) of the biological tissue and the antenna system as a whole, and thus temperature alone may be controlled in order to achieve desired ablation results, if desired, eliminating the steps of monitoring and controlling the reflected/forward power ratio. By establishing a temperature set point as measured and adjusting the RF frequency and the power delivered to the target tissue within the preset temperature set points, the tissue ablation process may be improved. In the representative embodiment illustrated in FIGS. 6 to 8, the combination of power ratio control and temperature control may increase effectiveness of the ablation system.

FIGS. 7 and 8 illustrate a control system and method which continuously monitors forward power, reflected power and temperature and adjusts both frequency and power levels to achieve and maintain lowest possible reflected/forward power ratio combined with near set point temperatures. The frequency and power level are set by micro-controller and firmware adjustment of the RF oscillator frequency and output level fed to the preamplifier-amplifier module 618. An ablation process starts with default values of frequency and power level and both are adjusted as necessary to achieve lowest ref/fwd power ratio and process temperature close to set point temperature. The system also has maximum limits for the power ratio, power level and temperature independent of the control loop and halts the process and alarms the user if the monitored readings exceed them.

The radio-frequency based catheter system and method for ablating biological tissues can be adapted to a variety of medical uses. The description and drawings contained herein represent some representative embodiments of the invention and are, as such, a representative of the subject matter which is broadly contemplated by the invention. The scope of the invention fully encompasses other embodiments that may become obvious to those skilled in the art, and the scope of the present invention is accordingly limited by nothing other than the appended claims.

What is claimed is:

1. A method for biological tissue ablation, comprising:
generating a train of radio frequency (RF) energy pulses at an output frequency and output power level for transmission in a transmission line to a RF antenna deployable adjacent to a biological tissue load;
detecting the reflected signal and the forward signal of the RF energy pulses when the RF antenna is placed adjacent to the biological tissue;
detecting the temperature at a temperature sensor associated with the antenna, and located adjacent the biological tissue;
comparing the detected temperature to a selected temperature setting;
adjusting the RF energy pulses to maintain a detected temperature at least close to the selected temperature setting; and
determining a reflected to forward power ratio based on the detected reflected and forward signals, and adjusting the RF energy pulses to maintain the lowest possible power ratio while maintaining the detected temperature at least close to the selected temperature setting.

2. The method of claim 1, wherein the reflected to forward power ratio comprises a voltage standing wave ratio (VSWR) based on the reflected signal and the forward signal.

3. The method of claim 2, wherein the output frequency and power level are adjusted such that the VSWR is below a preset threshold value while the detected temperature is at least close to the selected temperature setting.

4. The method of claim 1, further comprising amplifying the train of radio frequency (RF) energy pulses to control the power level.

5. The method of claim 1, further comprising sampling the forward signal and the reflected signal using a bi-directional coupler.

6. The method of claim 1, further comprising using a catheter to deploy the RF antenna to the biological tissue load.

7. The method of claim 1, further comprising accepting user input of the temperature setting and using the temperature setting selected by the user to control the RF energy pulses in order to maintain a detected temperature at least close to the user input temperature setting.

8. The method of claim 1, further comprising accepting user input of control parameters from a user and using the parameters in controlling the power ratio and detected temperature.

9. The method of claim 8, wherein the control parameters comprise at least a temperature set point and power level set point.

10. The method of claim 1, further comprising applying the train of RF energy pulses to the tissue load for a predetermined ablation time period while controlling the output frequency and power level of the pulses to achieve the desired power ratio and temperature.

11. The method of claim 1, further comprising setting a maximum limit for at least one output parameter comprising a selected one of the detected signals, the detected temperature, and the power ratio, monitoring said one output parameter during the ablation process, and halting the ablation process and providing a user alarm output if the maximum limit for said one output parameter is exceeded.

12. The method of claim 11, wherein the maximum limit comprises a maximum detected temperature.

13. The method of claim 11, wherein the maximum limit comprises a maximum power level.

14. The method of claim 11, wherein the maximum limit comprises a maximum reflected power to forward power ratio.

15. The method of claim 1, wherein the temperature setting is within the range from 45 degrees Celsius to 125 degrees Celsius.

16. The method of claim 1, wherein the biological tissue is heart tissue and the temperature setting is within a range from approximately 50 degrees to 90 degrees Celsius.

17. The method of claim 1, wherein the biological tissue is non-intracardiac tissue and the temperature setting is within a range from approximately 60 degrees to 120 degrees Celsius.

18. A system for biological tissue ablation, comprising:
 a radio frequency (RF) antenna for positioning adjacent a biological tissue site;
 a transmission line having a first end connected to the RF antenna and a second end;
 an RF signal generator adapted to generate a train of RF pulses in the transmission line for transmission to the RF antenna;
 a temperature sensor associated with the RF antenna;
 a controller connected to the RF signal generator and the temperature sensor and having a temperature control module configured to compare the detected temperature at the temperature sensor with a preset temperature setting, and a control module configured to adjust at least one parameter of the RF signal until the detected temperature is as close as possible to the preset temperature setting; and
 an RF signal detector coupled to the transmission line for detecting the reflected signal and the forward signal of the RF pulses, the controller having a processing module configured to calculate a ratio of the detected reflected signal to the detected forward signal of the RF pulses, the control module further being configured to control the RF signal generator to vary at least one parameter of the RF pulses until the calculated ratio substantially corresponds to a selected ratio which indicates a substantial match between transmission line impedance and RF antenna and biological tissue load impedance.

19. The system of claim 18, wherein the control module is configured to control the RF signal generator to vary the frequency and power level of the RF energy pulses in order to maintain the calculated ratio at least close to the selected ratio while maintaining the detected temperature at least close to the preset temperature setting.

20. The system of claim 19, wherein the selected ratio is the lowest achievable ratio.

21. The system of claim 19, wherein the selected ratio is a preset threshold value.

22. The system of claim 18, wherein the temperature setting is a temperature range.

23. The system of claim 18, wherein the temperature setting is a temperature set point plus or minus a predetermined amount.

24. The system of claim 18, further comprising an alarm device connected to the controller, the controller further comprising an alarm module configured to compare a detected temperature to a preset maximum temperature and to activate the alarm device to generate an alarm in the event that the detected temperature is above the preset maximum temperature.

25. The system of claim 24, wherein the controller is configured to turn off the RF signal generator if the detected temperature is above the preset maximum temperature.

26. The system of claim 24, wherein the controller is configured to compare a detected power level to a preset maximum power level and to activate the alarm device to generate an alarm in the event that the detected power level is above the preset maximum power level, the alarm module further being configured to turn off the RF signal generator if the power level exceeds the preset maximum power level.

27. The system of claim 18, further comprising a user input module connected to the controller, the user input module being configured for user input of user selected parameters.

28. The system of claim 27, wherein the user selected parameters comprise a temperature setting and an RF signal power level, the controller being further configured to maintain the RF signal as close as possible to the user selected power level while maintaining the selected temperature setting.

29. The system of claim 28, wherein the user selected parameters further comprise an ablation time period.

30. The system of claim 18, wherein the RF antenna is deflectable.

31. The system of claim 18, wherein the RF antenna is shapeable.

32. The system of claim 20, further comprising a catheter to deploy the RF antenna to the biological tissue load.

33. A system for biological tissue ablation comprising:
 an RF signal module configured to generate a train of radio frequency (RF) energy pulses for transmission in a transmission line to a RF antenna deployable adjacent to a biological tissue load;
 an RF sensor module configured to sense the reflected signal and the forward signal of the RF energy pulses when the RF antenna is placed adjacent to the biological tissue to be ablated;

a temperature sensor module configured to detect the temperature when the RF antenna is placed adjacent the biological tissue to be ablated; and a control module connected to the RF signal module, RF sensor module, and temperature sensor module and configured to adjust the train of RF energy pulses to maintain a ratio of reflected power to forward signal power at least close to a predetermined ratio and to maintain the detected temperature at least close to a pre-selected temperature setting.

34. The system of claim 33, wherein the control module is configured to determine the ratio of the reflected signal power to the forward signal power in the transmission line and the predetermined ratio is the lowest achievable ratio of reflected signal power to forward signal power while maintaining a detected temperature at least close to the selected temperature setting.

35. The system of claim 33, wherein the control module is configured to measure the voltage standing wave ratio (VSWR) and the predetermined ratio is a VSWR.

36. The system of claim 33, wherein the RF signal module comprises an RF oscillator module for producing a train of RF pulses and an amplifier module connected to the output of the oscillator module for amplifying the train of radio frequency (RF) energy pulses, and the control module is configured to control the oscillator module and the amplifier module to vary the pulse frequency and power level.

37. The system of claim 33, wherein the RF sensor module comprises a bidirectional signal detection module for sampling the forward signal and the reflected signal.

38. The system of claim 33, further comprising an elongate catheter configured for insertion into a body vessel and having a proximal end coupled with said RF signal module, a distal end portion containing said RF antenna for deploying adjacent a selected tissue site for ablation, a transmission line extending along said catheter from said proximal end to said RF antenna, the temperature sensor module comprising a temperature sensor at the distal end portion of said catheter and a connecting line extending along said catheter from said temperature sensor to said proximal end, said connecting line being connected to a temperature sensor input of said control module.

39. The system of claim 33, further comprising a user input module connected to said control module for receiving user control inputs from a user.

40. The system of claim 33, further comprising an alarm module for providing an alarm output on detection of sensor outputs above predetermined maximum limits.

41. A system for biological tissue ablation, comprising:
a radio frequency (RF) antenna for positioning adjacent a biological tissue site;
a transmission line having a first end connected to the RF antenna and a second end;
an RF signal generator adapted to generate a train of RF pulses, the RF signal generator having an output coupled to the second end of the transmission line;
an RF signal detector coupled to the transmission line for detecting the reflected signal and the forward signal of the RF pulses;
and a controller connected to the RF signal generator and the RF signal detector and having a processing module configured to calculate a voltage standing wave ratio (VSWR) of the detected reflected signal to the detected forward signal and a control module for controlling the RF signal generator to vary the frequency of the RF pulses until the calculated VSWR ratio substantially corresponds to a selected VSWR ratio which effects a substantial match of transmission line impedance with a tissue load impedance.

42. The system as claimed in claim 41, further comprising a temperature sensor associated with the RF antenna for positioning adjacent the biological tissue site, the controller having a temperature control module configured to compare the detected temperature at the temperature sensor with a preset temperature setting, and the control module further being configured to adjust the RE signal until the detected temperature is as close as possible to the preset temperature setting while maintaining the calculated ratio as close as possible to the selected ratio.

43. The system as claimed in claim 42 wherein the RF antenna is a shapeable antenna to accommodate the contour of a body vessel adjacent a biological tissue load.

* * * * *

UNITED STATES PATENT AND TRADEMARK OFFICE
CERTIFICATE OF CORRECTION

PATENT NO.       : 7,594,913 B2
APPLICATION NO.  : 11/479259
DATED            : September 29, 2009
INVENTOR(S)      : Ormsby et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this

Twenty-eighth Day of September, 2010

David J. Kappos
*Director of the United States Patent and Trademark Office*